(12) United States Patent
Garcia et al.

(10) Patent No.: US 11,744,732 B2
(45) Date of Patent: Sep. 5, 2023

(54) MEDICATION-COATED PATIENT INTERFACE DEVICE FOR OPHTHALMIC LASER SURGERY

(71) Applicant: AMO DEVELOPMENT, LLC, Santa Ana, CA (US)

(72) Inventors: Jose L. Garcia, Fremont, CA (US); Vye Chi Low, Milpitas, CA (US); Audrey Jonas, Palo Alto, CA (US)

(73) Assignee: AMO Development, LLC, Irvine, CA (US)

( * ) Notice: Subject to any disclaimer, the term of this patent is extended or adjusted under 35 U.S.C. 154(b) by 307 days.

(21) Appl. No.: 15/788,676

(22) Filed: Oct. 19, 2017

(65) Prior Publication Data

US 2019/0117455 A1 Apr. 25, 2019

(51) Int. Cl.
*A61F 9/00* (2006.01)
*A61F 9/007* (2006.01)
*B29C 45/00* (2006.01)
*B29C 45/26* (2006.01)
*A61F 9/009* (2006.01)
(Continued)

(52) U.S. Cl.
CPC ........ *A61F 9/0026* (2013.01); *A61F 9/00754* (2013.01); *B29C 45/0053* (2013.01); *B29C 45/263* (2013.01); *A61F 9/009* (2013.01); *B29C 2045/0079* (2013.01); *B29K 2083/00* (2013.01); *B29K 2101/12* (2013.01); *B29L 2031/7546* (2013.01)

(58) Field of Classification Search
CPC ........ A61F 9/0026; A61F 9/009; A61F 9/007; B29C 2045/0079
See application file for complete search history.

(56) References Cited

U.S. PATENT DOCUMENTS 6,863,667 B2 3/2005 Webb et al.
8,858,581 B2 10/2014 Robl et al.
(Continued)

FOREIGN PATENT DOCUMENTS

WO 2011155922 A1 12/2011
WO 2012162459 A1 11/2012
WO 2013070423 A1 5/2013

OTHER PUBLICATIONS

International Search Report for Application No. PCT/US2018/056198, dated Jan. 22, 2019, 6 pages.

*Primary Examiner* — Adam Marcetich
*Assistant Examiner* — Meagan Ngo
(74) *Attorney, Agent, or Firm* — Johnson & Johnson Surgical Vision, Inc.

(57) ABSTRACT

A patient interface device for use in ophthalmic surgery, which includes a rigid body and a suction ring joined to a lower end of the body, where the suction ring includes an annular skirt made of a soft and flexible material and located at a lower end of the suction ring, and where an inner surface, and optionally an outer surface, of the skirt is coated with medication. The medication includes one or more of the following types of medication: anti-inflammatory, antibiotic, numbing, lubricating, and anti-redness. The coating method may include dip coating, sputter deposition, ultrasonic-spraying, and spin-coating. The skirt may be formed by a process that increases its material porosity and/or surface roughness, and may be surface-treated to enhance adhesion and retention of the medication.

12 Claims, 2 Drawing Sheets

(51) Int. Cl.
    *B29K 83/00*     (2006.01)
    *B29K 101/12*     (2006.01)
    *B29L 31/00*     (2006.01)

(56) References Cited

U.S. PATENT DOCUMENTS

| | | |
|---|---|---|
| 9,044,302 B2 | 6/2015 | Gooding et al. |
| 10,105,927 B1* | 10/2018 | Varma ................ B32B 27/302 |
| 2004/0087902 A1* | 5/2004 | Richter ................ A61M 25/10 |
| | | 604/103.02 |
| 2004/0260254 A1 | 12/2004 | Neilson et al. |
| 2007/0122353 A1* | 5/2007 | Hale ................... A61K 9/0004 |
| | | 424/46 |
| 2008/0097591 A1* | 4/2008 | Savage ................ A61L 31/10 |
| | | 623/1.43 |
| 2008/0103367 A1* | 5/2008 | Burba ................. A61F 9/007 |
| | | 600/236 |
| 2010/0036488 A1* | 2/2010 | de Juan, Jr. ......... A61F 2/142 |
| | | 623/5.16 |
| 2010/0082072 A1* | 4/2010 | Sybert ................ A61B 17/68 |
| | | 606/326 |
| 2014/0094759 A1* | 4/2014 | Mansfield ........... A61F 9/0008 |
| | | 604/290 |
| 2014/0216468 A1 | 8/2014 | Goldshleger et al. |
| 2014/0275751 A1* | 9/2014 | Heitel ................. A61F 9/009 |
| | | 600/37 |
| 2014/0276673 A1* | 9/2014 | Heitel ................. A61F 9/009 |
| | | 606/4 |
| 2014/0364789 A1* | 12/2014 | Schaller ............. A61F 9/00781 |
| | | 604/8 |
| 2015/0125701 A1* | 5/2015 | Kieslich ............. B29C 45/16 |
| | | 428/412 |
| 2015/0352771 A1* | 12/2015 | Tzor ................... B29C 49/28 |
| | | 428/35.7 |
| 2016/0074220 A1* | 3/2016 | Ianchulev .......... A61F 9/00763 |
| | | 606/107 |
| 2019/0105264 A1* | 4/2019 | Higuchi ............. A61F 9/0008 |

* cited by examiner

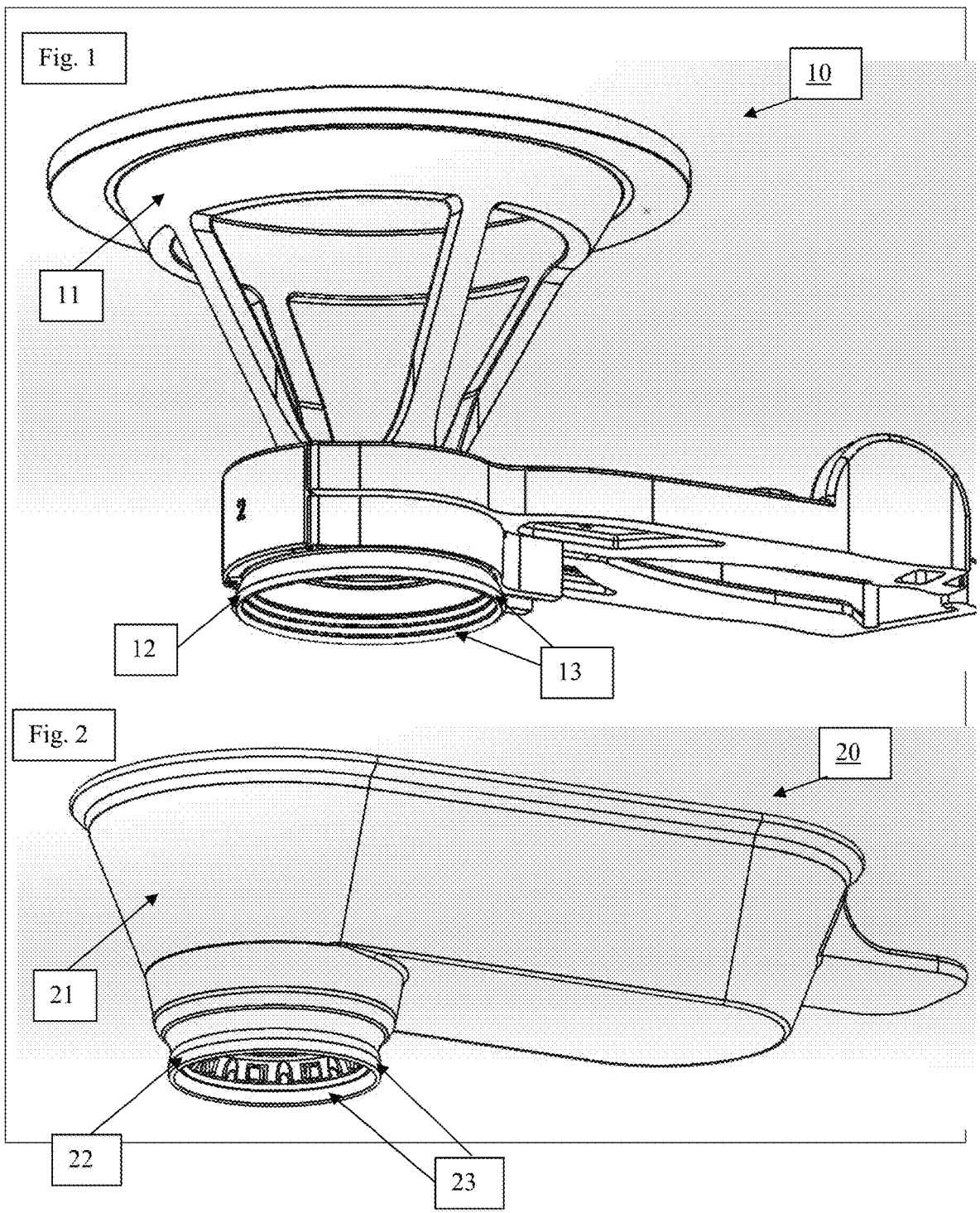

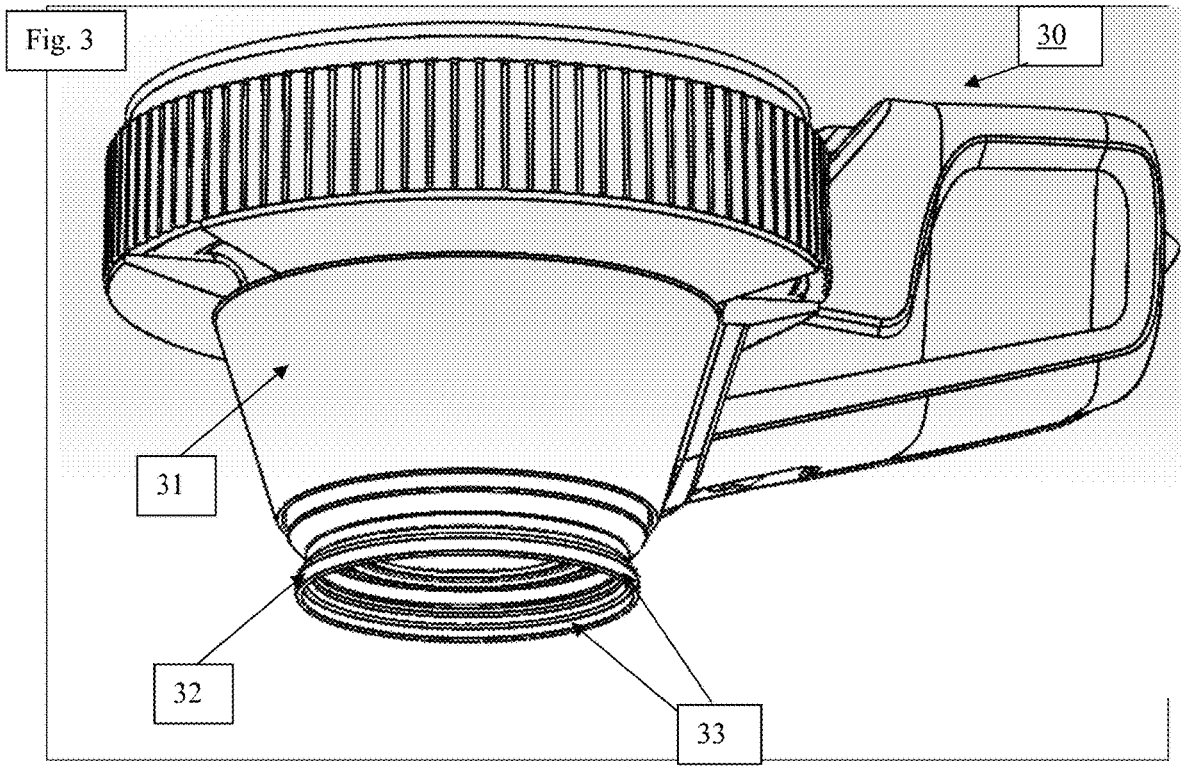
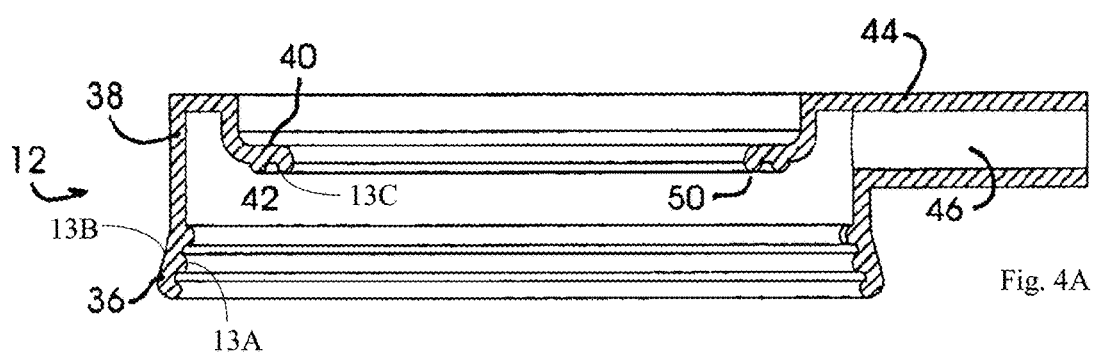
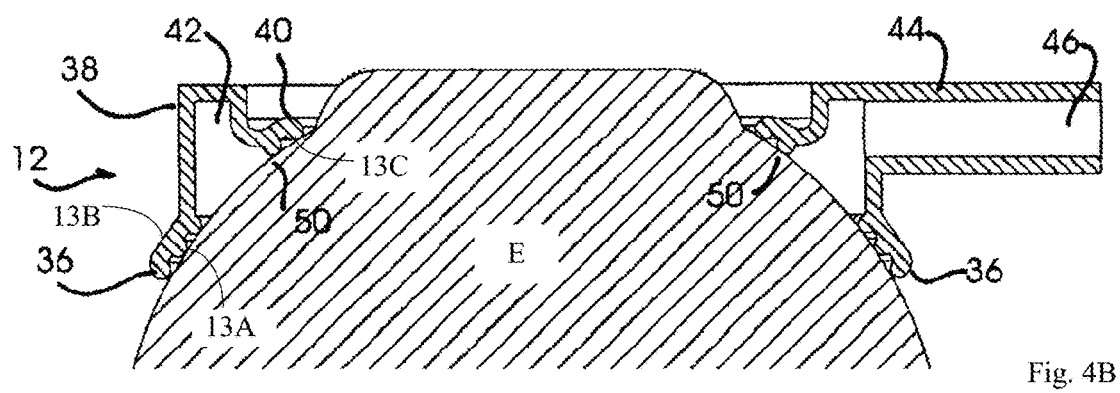

MEDICATION-COATED PATIENT INTERFACE DEVICE FOR OPHTHALMIC LASER SURGERY

BACKGROUND OF THE INVENTION

Field of the Invention

Embodiments of this invention generally relate to a patient interface device for ophthalmic laser surgeries, and in particular, it relates to patient interface device for ophthalmic laser surgeries having a contact surfaces coated with medication.

Description of Related Art

Significant developments in laser technology have led to its application in the field of ophthalmic surgery, and laser surgery has become the technique of choice for ophthalmic surgical applications. Ophthalmic surgery is a precision operation and requires precise coupling between the surgical tool (i.e., the laser beam) and the region to be surgically altered (i.e., a portion of the patient's eye). Movement of the eye with respect to the intended focal point of the laser beam can lead to non-optimal results and could even result in permanent damage to tissue within the eye. Given that eye movement is often the result of autonomic reflex, techniques have been developed in an attempt to stabilize the position of a patient's eye with respect to an incident laser beam.

Mechanical stabilization devices, referred to as patient interface (PI) devices, have been developed for coupling the patient's eye to the laser system. A PI typically has a component that directly contacts the eye, and engages and stabilizes the eye; meanwhile, the PI is attached to the laser system, so that the laser beam can be aligned to the eye. Conventional designs of PIs typically have either a one-piece or a two-piece structure. For example, U.S. Pat. Nos. 6,863,667 and 9,044,302 disclose various PI devices. A single-piece PI, or the piece of a two-piece PI that contacts the eye, is typically a single-use item intended to be used only once.

SUMMARY

During laser ophthalmic procedures, such as LASIK or cataract surgeries, certain conditions such as pain, inflammation, dry eyes, and/or an increase in intraocular pressure may occur. These problems may further cause post-operative conditions such as dry eyes, inflammation, pain, infection, etc. Conventionally, these conditions are addressed by administering eye drops with medication before, during, and/or after the procedure. Additionally, sedatives are sometimes administered (e.g. orally) pre-operative, and painkillers are sometimes administered post-operative.

Embodiments of the present invention provide a solution to the above problems by using a patient interface (PI) device having surfaces coated with medication (drug). More specifically, a suction ring of the PI which directly contacts the eye during the procedure is coated with medication intended to treat any of the previously mentioned conditions. The medication is thus delivered to the patient's eye from the PI during the procedure, which can reduce the amount of eye drops that would be required before, during or after the procedure, and can thus streamline the workflow during surgery.

In one aspect, the present invention provides a patient interface device for use in ophthalmic surgery, which includes: a rigid body; and a suction ring joined to a lower end of the body, wherein the suction ring includes an annular skirt made of a soft and flexible material and located at a lower end of the suction ring, and wherein at least an inner surface of the skirt is coated with medication. An outer surface of the skirt may also be coated with medication.

In another aspect, the present invention provides a method for forming a patient interface device for use in ophthalmic surgery, which includes: forming a rigid body and a suction ring joined to a lower end of the body, wherein the suction ring includes an annular skirt made of a soft and flexible material and located at a lower end of the suction ring; and coating at least an inner surface of the skirt with medication. The coating step may include one of: dip coating, sputter deposition, ultrasonic-spraying, and spin-coating.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

FIGS. 1, 2 and 3 each illustrates a patient interface device according to embodiments of the present invention.

FIGS. 4A and 4B illustrate the structure of a suction ring of a patient interface device according to an embodiment of the present invention.

DETAILED DESCRIPTION OF PREFERRED EMBODIMENTS

Embodiments of the present invention provide a patient interface (PI) device having surfaces coated with medication. More specifically, a portion of the polymeric suction ring of the PI which directly contacts the eye during the procedure is coated with medication. The medication is delivered to the patient's eye from the PI during the procedure. The medication may be one of, or a combination of two or more of, the following types of medication: anti-inflammatory, antibiotic, numbing, lubricating, and anti-redness.

FIG. 1 illustrates an exemplary PI device 10, which includes a suction ring with a soft and flexible skirt 12 formed of a polymeric material. During surgery, the skirt of the suction ring contacts and engages the anterior surface of the eye. Structural details of the PI device 10 are disclosed in U.S. Pat. No. 6,863,667, titled Ocular Fixation and Stabilization Device for Ophthalmic Surgical Procedures, in particular, FIGS. 5 and 6, which show cross sectional views of the PI. This patent is herein incorporated by reference in its entirety. In this embodiment of the present invention, surfaces 13 (both inside and outside) of the skirt 12 are coated with medication.

FIG. 2 illustrates another exemplary PI device 20, which includes a suction ring with a soft and flexible skirt 22 formed of a polymeric material. During surgery, the skirt of the suction ring contacts and engages the anterior surface of the eye. Structural details of the PI device 20 are disclosed in U.S. Prov. Appl. No. 62/414,605, titled Patient Interface Device for Ophthlamic Surgical Laser System, in particular, its FIGS. 5 and 6, which show cross sectional views of the PI. This patent application is herein incorporated by reference in its entirety. In this embodiment of the present invention, surfaces 23 (both inside and outside) of the skirt 22 are coated with medication.

FIG. 3 illustrates another exemplary PI device 30, which includes a suction ring with a soft and flexible skirt 32 formed of a polymeric material. During surgery, the skirt of the suction ring contacts and engages the anterior surface of the eye. Structural details of the PI device 30 are disclosed in U.S. Pat. No. 9,044,302, titled Patient Interface for Ophthalmic Diagnostic and Interventional Procedures, in particular, FIGS. 7A, 7L, which show a perspective view of the PI and a cross sectional view of the skirt. This patent is herein incorporated by reference in its entirety. In this embodiment of the present invention, surfaces 33 (both inside and outside) of the skirt 32 are coated with medication.

The PIs shown in FIGS. 1, 2 and 3 are exemplary only; other PI designs may be used. More generally, the PI includes a rigid body (e.g. 11, 21, 31 shown in FIGS. 1, 2, 3), which may be formed of any suitable material such as plastic or metal, and an annular suction ring (e.g. 12, 22, 32 shown in FIGS. 1, 2, 3) joined to the lower end of the body. The suction ring may be formed separately from the body and attached to the body, for example by an adhesive or by a clamp. The suction ring has an annular shaped lower skirt (also denoted 12, 22, 32 in FIGS. 1, 2, 3) made of a soft and flexible material, e.g., silicone, thermoplastic elastomer (TPE), etc. which functions as a shroud that comes into intimate contact with the anterior portion of the eye during the ophthalmic procedure. The skirt has a relatively thin cross-section and is deformable so as to establish and maintain conformal contact with the anterior surface of the eye. The other portion of the suction ring may be made of the same material as the skirt or a different (e.g. more rigid) material.

Detailed structures of the suction ring 12 of the PI device of FIG. 1 is illustrated in FIGS. 4A and 4B, which are adapted from FIGS. 5 and 6 of the above-mentioned U.S. Pat. No. 6,863,667. FIG. 4A shows the suction ring 12 before it is applied to the patient's eye; FIG. 4B shows the suction ring applied to the patient's eye E. The suction ring 12 has an upper portion including a side wall 38, a lower shroud portion (skirt) 36, and an inner annular member 40; the suction ring defines an annular channel 42 which forms a sealed space when the suction ring is applied to the patient's eye such that the lower shroud portion 36 and the contact edge 50 of the inner annular member 40 are in contact with the anterior surface of the eye. A vacuum pressure may be applied to the channel 42 via an orifice 46 and a tubing in an attachment fitting 44 of the PI, to securely attach the suction ring to the eye.

In some embodiments, medication is coated on the suction ring 12 at some or all the following locations: the inside surface 13A of the skirt 36, the outside surface 13B of the skirt, and the inside surface 13C (i.e. the contact edge 50) of the inner annular member 40. The outer surface of the side wall 38 may also be coated with medication. Depending on the coating method, it may be convenient to coat substantially all of the exposed surface areas of the suction ring 12 (or 22, 32) with medication.

One advantage for coating medication on the outside surface 13B of the skirt is that, even though the outside surface is not in contact with the surface of the eyeball E, it is often in contact with the eyelid during surgery, so that medication may be delivered to the eyelid as desired. In some embodiments, the inside surface 13A and the outside surface 13B of the skirt may be coated with different medication or different combinations of medication.

In some other embodiments, the suction ring only has one annular skirt that contacts the anterior surface of the eye, i.e., it does not have a structure similar to the inner annular member 40 shown in FIGS. 4A and 4B that contacts the surfaces of the eye. When placed on the eye, a vacuum pressure is maintained in a volume enclosed by the skirt, the surface of the eye, and other components of the PI device to secure the suction ring to the eye.

The amount of medication coated on the suction ring skirt may be determined based on practical need.

Any suitable coating method may be employed to coat the medication on the surfaces of the suction ring, including, without limitation: dip coating, sputter deposition, ultrasonic-spray, and spin-coating.

In a dip coating method, the PI suction ring skirt is dipped into the drug coating solution and is withdrawn from the solution after a set amount of time at a controlled speed.

In a sputter deposition method, the PI is placed into a chamber where the drug coating materials ejected via ion or atom bombardment are deposited on the PI suction ring skirt (indirect application of drug).

In an ultrasonic-spraying method, the PI is placed into a chamber where atomized particles of drug coating solution are supplied (direct application of drug).

In a spin-coating method, a small amount of the drug coating solution is applied in the U-portion of the suction ring skirt and the PI unit is rotated at high speed in order to spread the drug coating up to the tips of the suction ring skirt.

Further, the PI suction ring skirt may be prepped for drug adhesion, retention, or saturation via appropriate methodologies.

For example, in a first method, the porosity of the thermoplastic elastomer (TPE) material that forms the suction ring skirt is altered. The following factors impact the material porosity during manufacturing: melt fix time, moisture, and backpressure. The injection molding process may be optimized to deliver a more porous TPE material on the suction ring skirt by decreasing screw speed or backpressure of each shot, increasing moisture levels, or decreasing mold temperature during processing. A PI suction skirt made of a more porous material may better absorb drug molecules when exposed. In one embodiment, the porosity of the suction skirt is about 12-30%.

In a second method, the surface roughness and surface area of the TPE material that forms the suction ring skirt are altered. The surface of the suction ring skirt may be altered by texturizing the mold to increase surface roughness and surface area for drug adhesion. Increasing the surface roughness allows increased rates of molecular attractive interactions including ionic, static, polar, and van der Waals forces. Texturizing the surface also increases bonding ability by providing a larger bonding surface area. In one embodiment, the surface roughness is of Ra value of between 0.8 μm to 25 μm.

In a third method, surface modification techniques are used to change the chemical composition of the TPE material to increase its affinity for drug bonding. Surface energy is the work per unit area done by the force that creates the new surface. A lower surface energy material will spontaneously "wet out" or cover a higher energy surface. Therefore, the drug to be bonded needs to have lower surface energy than the PI skirt. One technique that may be used to increase the surface energy of a surface is plasma treatment. Thus, the PI unit may be placed in a plasma oven with the suction skirt surface exposed, be treated for a desired amount of time, and then immediately exposed to the drug via the coating methods described above.

Alternatively, instead of or in addition to being coated on the surface of the suction ring skirt, medication may be suspended in the polymer matrix and/or hydro-gel matrix that forms the suction ring skirt or other parts or the PI that contact the patient.

It will be apparent to those skilled in the art that various modification and variations can be made in the medication-coated PI devices of the present invention without departing from the spirit or scope of the invention. Thus, it is intended that the present invention cover modifications and variations that come within the scope of the appended claims and their equivalents.

What is claimed is:

1. A patient interface device for use in ophthalmic surgery, comprising:
    a rigid body; and
    a suction ring joined to a lower end of the body,
    wherein the suction ring includes an annular skirt made of a soft and flexible thermoplastic elastomer (TPE) material and located at a lower end of the suction ring, wherein the TPE material has a texturized surface with a surface roughness value between 0.8 m to 25 um, and
    wherein an inner surface of the annular skirt is coated with a first medication and an outer surface of the annular skirt is coated with a second medication.

2. The patient interface device of claim 1, wherein the first or second medication includes one or more of: anti-inflammatory medication, antibiotic medication, numbing medication, lubricating medication, and anti-redness medication.

3. The patient interface device of claim 1, wherein the second medication coated on the outer surface and the first medication coated on the inner surface of the annular skirt are different medications.

4. The patient interface device of claim 1, wherein the TPE material has a porosity of about 12-30%.

5. The patient interface device of claim 1, wherein the annular skirt is made of a plasma-treated thermoplastic elastomer (TPE) material.

6. A method for forming a patient interface device for use in ophthalmic surgery, comprising:
    forming a rigid body and a suction ring joined to a lower end of the body,
    wherein the suction ring includes an annular skirt made of a soft and flexible thermoplastic elastomer (TPE) material and located at a lower end of the suction ring, including forming the annular skirt by injection molding using a texturized mold, wherein the annular skirt has a surface roughness value between 0.8 um to 25 um; and
    coating an inner surface of the annular skirt with a first medication and an outer surface of the annular skirt with a second medication.

7. The method of claim 6, wherein the coating step includes one of: dip coating, sputter deposition, ultrasonic-spraying, and spin-coating.

8. The method of claim 6, further comprising, before the coating step: prepping the inner surface of the skirt to increase adhesion and retention of the medication.

9. The method of claim 6, wherein the first or second medication includes one or more of: anti-inflammatory medication, antibiotic medication, numbing medication, lubricating medication, and anti-redness medication.

10. The method of claim 6, wherein the second medication coated on the outer surface and the first medication coated on the inner surface of the annular skirt are different medications.

11. The method of claim 6, wherein the TPE material has a porosity of about 12-30%.

12. The method of claim 6, further comprising: prior to coating, plasma-treating the annular skirt.

* * * * *